United States Patent [19]

Dillman

[11] 3,978,732

[45] Sept. 7, 1976

[54] SAMPLING SYSTEM FOR POWER GENERATORS

[75] Inventor: Thayer L. Dillman, North Versailles, Pa.

[73] Assignee: Westinghouse Electric Corporation, Pittsburgh, Pa.

[22] Filed: Aug. 1, 1975

[21] Appl. No.: 601,579

[52] U.S. Cl. ............................................ 73/421.5 R
[51] Int. Cl.² ........................................ G01N 1/22
[58] Field of Search ................ 73/28, 421.5 R, 432; 55/350

[56] References Cited
UNITED STATES PATENTS

| | | | |
|---|---|---|---|
| 3,174,326 | 3/1965 | Carle et al. ............................ | 73/23.1 |
| 3,490,205 | 1/1970 | Hauser .................................. | 55/350 |
| 3,702,561 | 11/1972 | Carson et al. ........................ | 73/1 F |
| 3,807,218 | 4/1974 | Carson et al. ........................ | 73/28 |

Primary Examiner—S. Clement Swisher
Attorney, Agent, or Firm—G. H. Telfer

[57] ABSTRACT

A system for automatically monitoring and sampling thermally decomposed products entrained in a gas stream coolant of a power generator. If a gas stream monitoring device detects the presence of thermally decomposed products of a generator in the gas stream coolant, then a single sample is taken on a primary sampler. Should additional samples be necessary, there is provided one or more secondary samplers associated with devices that record the number of samples taken, the total volume of the coolant sampled, and the time the samples were taken. The products collected can be analyzed to determine which material in the power generator was thermally decomposed.

9 Claims, 1 Drawing Figure

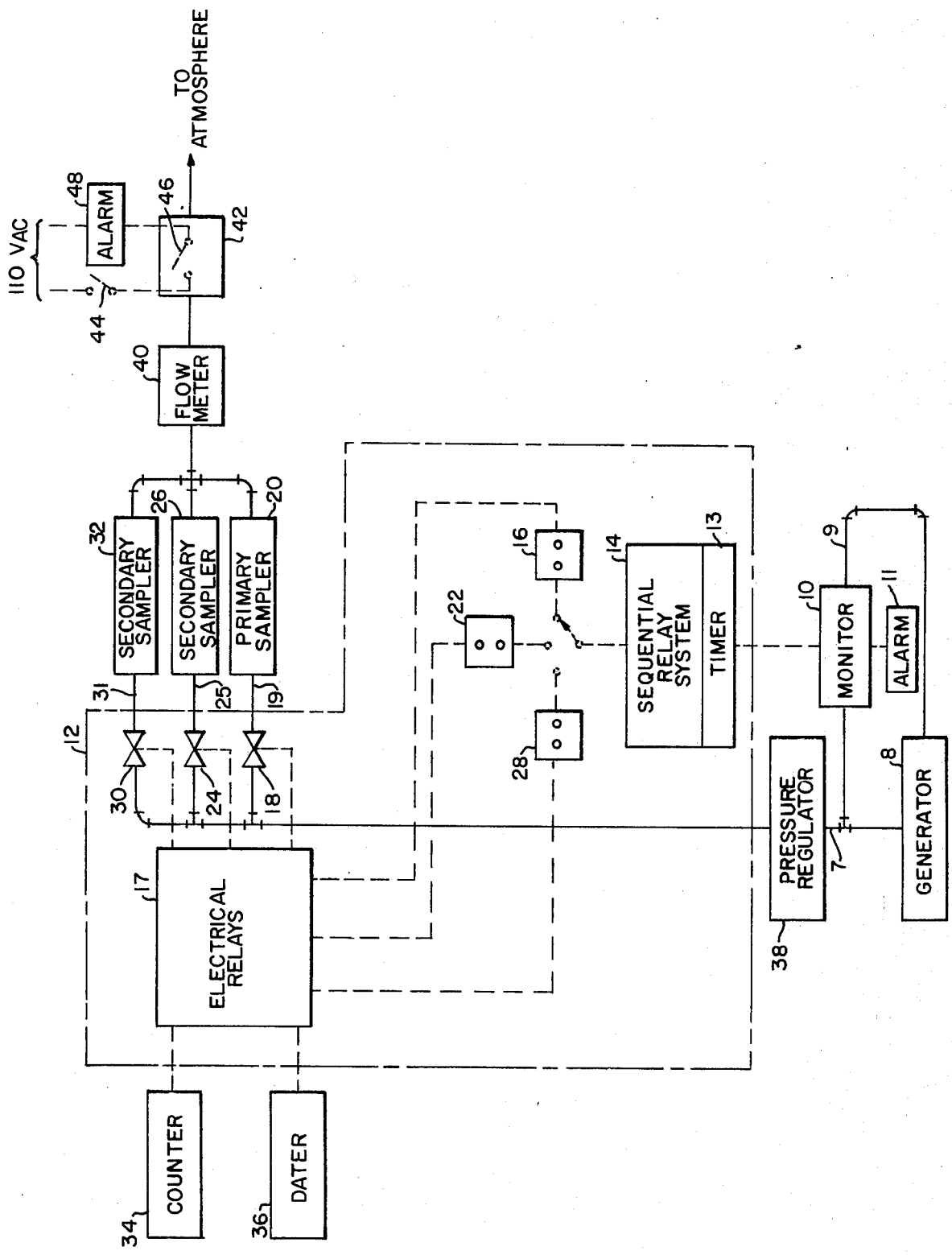

SAMPLING SYSTEM FOR POWER GENERATORS

BACKGROUND OF THE INVENTION

This invention relates to an improved arrangement for detecting and sampling the decomposition products entrained in the coolant of a generator for the purpose of locating the source of the products.

Power generators occasionally fail due to localized overheating of their internal parts. The delay in locating the failure can result in great expense due to repair cost and long periods of down time. The overheating causes the organic coatings of the overheated parts to decompose giving off submicron products which are entrained in the coolant of the generator.

In U.S. Pat. No. 3,427,880, to Grobel et al., issued Feb. 18, 1969, there is described a system for the detection of overheating in a dynamoelectric machine. In that system the components for which overheating is to be detected are coated with a substance that produces submicron decomposition products at an ascertained temperature. A gas coolant which entrains the products is circulated through an ion chamber detector which detects the presence of the decomposed products. The Grobel et al. patent is concerned only with the detection of the presence of the products. However, since materials other than the coating substance may decompose, it is also desirable to be able to determine which substance decomposed and from where that substance came.

In U.S. Pat. No. 3,807,218, to Carson et al., issued Apr. 30, 1974, there is described a system for detecting and sampling products of thermal decomposition in a gas cooled dynamoelectric machine. In that system the coolant of the dynamoelectric machine is continuously monitored by an ion chamber detector. If the monitor detects these products, a valve system allows flow to a sampler which separates these products from the coolant. The sampler is removed and the sample is subjected to mass spectrometric or gas chromatographic analysis. From the analysis, it is possible to determine from which type of coating the product came. By knowing the coating of each part of the generator, the location of the overheating can be determined which greatly reduces the time necessary to repair the generator. It is also possible to coat the various generator parts with materials that decompose before there is serious damage to the parts thereby avoiding a failure of the part.

In copending application Ser. No. 426,391 filed Dec. 19, 1973 by Fort et al and assigned to the present assignee, there is described a system for automatically sampling a gas stream in response to a signal from the monitor that has been checked for its authenticity. The copending application also describes an improved sampling device.

Occasionally, either by accident or by necessity, multiple samples are taken on a sampler. Although the prior art describes a method for taking a sample, it does not solve the problem of taking multiple samples at different times and under different circumstances without obscuring the results of any individual sample.

SUMMARY OF THE INVENTION

The invention is a system for automatically monitoring and sampling thermally decomposed products entrained in a gas stream coolant of a power generator. When the monitoring device detects the presence of thermally decomposed products of the generator in the gas stream coolant, a single sample is taken on a primary sampler. The products collected may then be analyzed to determine which material in the power generator was thermally decomposed. In the event of either false alarms, a genuine alarm while the primary sampler is being changed, or the necessity of taking multiple samples where a first sample has been collected and the sampler not replaced with a fresh one, one of the secondary samplers is activated by the valving system in such a manner as to insure that only a single sample is taken on the primary sampler. In addition, a system associated with taking multiple samples on the secondary samplers is provided for recording the number of samples taken, the total volume of the coolant sampled, and the time the samples were taken.

While particularly directed to monitoring and sampling thermal decomposition products in gas cooled generators it will be apparent that in its broader aspects the invention may be applied to monitoring and sampling products in other systems with a circulating fluid.

BRIEF DESCRIPTION OF THE DRAWING

The single FIGURE of the drawing is a schematic diagram of one embodiment of the present invention. The solid lines indicate the coolant paths while the dashed lines indicate electrical connections.

DESCRIPTION OF THE PREFERRED EMBODIMENTS

Referring to the drawing, a gas stream coolant which has circulated through a generator 8, continuously flows through the conduit 9 to the monitor 10. Generally, this coolant is clean hydrogen gas. However, when local overheating of generator parts occur, the coatings of these parts decompose. The coatings referred to may be normally present paint or insulating material or may be specially provided "sacrificial" coatings applied to machine elements to produce thermal decomposition products before any of the normally present materials are affected. The circulating coolant entrains these decomposition products and carries them through the system by the main path or conduit 9.

A typical suitable monitor comprises an ion chamber detector as in above-mentioned U.S. Pat. No. 3,427,880. The detector consists of an ionizing section and an ion collecting chamber contained in a pressure housing. The coolant flow passes through the ionizing section which incorporates a low level ion source. The ions are carried by the coolant to the ion collecting chamber that contains a collector and an electrode. Because of their high electrical mobility, most of the ions are attracted to the collector, producing a current. However, when due to overheating, decomposition products are present in the coolant, some of the ions become attached to them, creating particle-ion combinations with a very greatly reduced charge-to-mass ratio. Since their electrical mobility is extremely low, only a few of the particle-ion combinations are attracted to the collector, resulting in a significant decrease in collector current. When the current falls below a predetermined level, the monitor responds such as by activating alarm 11 which simultaneously alerts personnel of generator overheating.

The monitor also activates electrically operable valving means 12 which during a first time period allows the coolant to flow into a first sampler which may be of the type described in the above-mentioned copending application Ser. No. 426,391. During subsequent time periods the valving means prevents flow to the first sampler and allows flow to a system of multiple samplers in flow paths parallel to the flow path of the first sampler.

More specifically, the monitor signals a timer 13 and a sequential relay system 14 (SRS). In response to an initial alarm, the SRS routes a signal to the signal light control 16 which in turn relays a signal through electrical relays 17 opening valve 18 and allowing flow of the coolant to the primary sampler 20 on path or conduit 19. After a predetermined volume of coolant has been sampled on the primary sampler, valve 18 is closed and the SRS switches to the signal light control 22. When the primary sampler is replaced, all of the controls in the system are reset to their initial positions. If a second alarm occurs before the primary sampler has been replaced, the SRS relays the signal through the signal light control 22 opening valve 24 and allowing the sample to be taken on the secondary sampler 26 on path or conduit 25. After a sample is taken on sampler 26, valve 24 is closed and the SRS switches to the signal light control 28. Should additional multiple samples be necessary, the SRS relays a signal through signal light control 28 opening valve 30 and taking all additional samples on the secondary sampler 32 in path 31. Besides relaying signals from the SRS, each of the signal light controls has a light that when energized indicates that a sample is being taken on its respective sampler and has another light that when energized indicates that the sample is completed and that its respective sampler should be replaced. Each time a sample is taken, a counter 34 records the number of samples taken on each sampler, and a dater 36 records when and for how long the sample was taken.

Due to piping pressure losses and generator pressure variations, the coolant flow rate in the conduit 9 would vary. The pressure regulator 38 assures that there is constant pressure and, therefore, constant flow in the conduit 7 leading to the parallel paths 19, 25 and 31 that contain the samplers. Because the timer 13 regulates the duration of taking each sample, i.e., by supplying a signal after a certain interval to close the valve to the sampler in use and the pressure regulator 38 guarantees constant flow, the volume of coolant sampled during each sample is determined. However, should it become necessary to check the volume of flow through the samplers, a flow meter 40 is provided connected to each sampler in a manner to measure the flow through the samplers.

Should one of the valves (18, 24, 30) not close due to some malfunction of the components which might not be detected by operating personnel, the coolant flow would activate flow sensor 42. Flow sensor 42 consists of a switch 44, a switch 46 and an alarm 48 connected in series to 110 volts AC. Switch 44 which is normally closed, would be opened by appropriate relays (not shown) when a sample is being taken on any sampler. Switch 46 which is normally opened would be closed by the flow of coolant through the sensor. Alarm 48 only operates when both switches 44 and 46 are closed; therefore, alarm 48 is only activated when there is flow through the sensor while no sample is being taken. It is to be noted, that a sensor that responds to the presence of hydrogen may be used in place of the flow sensor.

When a sample is taken, each sampler separates the decomposition products from the coolant. The sampler is then removed so that the sample of products may be analyzed. Analysis of the products, which may be by mass spectrometric or gas chromatographic analysis, will disclose from what type of coatings the products came. By knowing the type of coatings on the various parts of the generator, it is then possible to determine from which part of the generator the products came and thus determine the location of the overheating in the generator.

Because the main function of the primary sampler is to take a first and only one sample, it was previously envisioned that the primary sampler be changed after each sample. In other systems, the failure to replace the sampler before an additional sample is taken on that sampler would obscure the results of any individual sample. However, in the event of either false alarms, a genuine alarm while the primary sampler is being changed, or the necessity of taking multiple samples, the present invention provides a means whereby the secondary samplers are activated in a manner to ensure that only a single sample is taken on the primary sampler. Furthermore, the secondary samplers provide the capability of taking additional single or multiple samples while recording the number of samples taken, the total volume of the coolant sampled, and the time the samples were taken.

While there is described what is now considered to be the preferred embodiment of the invention, it is, of course, understood that various other modifications may be made therein; and it is intended to claim all such modifications as fall within the true spirit and scope of the present invention. For instance, as an alternative to the present embodiment, the three valves may be replaced by one that directs the flow into the appropriate conduit. Also, the valves, counter, and timer could be made flow responsive rather than responsive to the monitor. In addition, it can be seen that different types of samplers can be used in various arrangements to yield a variety of results. Likewise, it is believed that the electrical relays, associated components, and the manner of their interconnection may be readily selected from among those that are well known in the controls art.

I claim:

1. A monitoring and sampling system for a fluid subject to introduction of detectable products of deterioration of the fluid enclosure comprising:
   a monitor located in the flow path of said fluid and responsive to a predetermined concentration of said detectable products in said fluid;
   a primary sampler located in a second flow path of said fluid for collecting a single sample by separating said detectable products from said fluid;
   at least one secondary sampler located in a third flow path parallel to said second flow path for collecting at least one additional sample in same manner as said primary sampler;
   valve means responsive to said monitor for permitting flow of said fluid through said primary sampler and not through said secondary sampler during a first time period in which said monitor is detecting said products and through said secondary sampler and not through said primary sampler during a subsequent time period.

2. The system recited in claim 1 wherein said system further includes:
   apparatus responsive to a signal from said monitor for recording the number of said samples taken, the total volume of said fluid sampled, and the time said samples were taken.

3. The system recited in claim 1 wherein said fluid is a gas stream coolant from a dynamoelectric machine.

4. The system recited in claim 2 wherein said system further includes a flow sensor associated with said samplers for detecting malfunctioning of said valves.

5. The system recited in claim 2 wherein said apparatus is responsive to flow through said sampler.

6. A monitoring and sampling system for detection and analysis of thermally decomposed products entrained in a gas stream coolant of a dynamoelectric machine comprising:
- a monitor located in a first flow path of said coolant and responsive to a predetermined concentration of said thermally decomposed products in said coolant;
- a primary sampler located in a second flow path parallel to said first flow path of said coolant, for collecting a single sample by separating said detectable products from said coolant;
- at least one secondary sampler located in a third parallel flow path of said coolant for collecting at least one additional sample in same manner as said primary sampler;
- valve means responsive to said monitor for permitting flow of said coolant through said primary sampler and not through said secondary sampler during a first time period in which said monitor is detecting said products and through said secondary sampler and not through said primary sampler during a subsequent time period.

7. The system recited in claim 6 wherein said system further includes:
- apparatus responsive to a signal from said monitor for recording the number of said samples taken, the total volume of said coolant sampled, and the time said samples were taken;
- means indicating said primary sampler has taken said single sample, said means being deactivated only by replacing said primary sampler.

8. The system recited in claim 7 wherein said system further includes a flow switch associated with said samplers for detecting malfunctioning of said valves.

9. The system recited in claim 7 wherein said apparatus is responsive to flow through said sampler.

* * * * *